United States Patent [19]

Southwell et al.

[11] Patent Number: 5,100,233
[45] Date of Patent: Mar. 31, 1992

[54] REFRACTIVE INDEX MONITOR FOR DEPOSITION OF GRADIENT-INDEX FILMS

[75] Inventors: William H. Southwell, Thousand Oaks; Kirkpatrick W. Norton, San Diego, both of Calif.

[73] Assignee: Rockwell International Corporation, El Segundo, Calif.

[21] Appl. No.: 411,069

[22] Filed: Sep. 22, 1989

[51] Int. Cl.$^5$ .................. G01N 21/41; G01B 11/06
[52] U.S. Cl. .................................. 356/128; 356/382
[58] Field of Search ............... 356/128, 132, 361, 355, 356/381–382; 350/164, 166; 427/10, 162, 167, 38–39; 118/719, 726, 727; 250/560, 571

[56] References Cited

U.S. PATENT DOCUMENTS

| | | | |
|---|---|---|---|
| 3,751,162 | 8/1973 | Long | 356/128 |
| 3,975,097 | 8/1976 | Minto | 356/128 |
| 4,335,961 | 6/1982 | Chou et al. | 356/128 |
| 4,583,822 | 4/1986 | Southwell | 350/164 |
| 4,676,646 | 6/1987 | Strand et al. | 356/381 |
| 4,680,084 | 7/1987 | Heimann et al. | 356/382 |
| 4,707,611 | 11/1987 | Southwell | 250/560 |
| 4,778,251 | 10/1988 | Hall et al. | 350/166 |
| 4,787,749 | 11/1988 | Ban et al. | 356/382 |
| 4,837,044 | 6/1989 | Murarka et al. | 427/762 |

OTHER PUBLICATIONS

Macleod, H. A., *Thin-Film Optical Filters*, 2d Ed., pp. 423–445 (MacMillan, 1986).

Primary Examiner—Vincent P. McGraw
Assistant Examiner—Hoa Pham
Attorney, Agent, or Firm—John C. McFarren

[57] ABSTRACT

A method is provided for monitoring the refractive index of an optical film as it is being deposited on a substrate. The film is illuminated by a source of light at a wavelength that is outside and less than the reflectance band of the coating. If the refractive index of the film is initially matched to the refractive index of the substrate and has no abrupt changes in its gradient-index profile, reflectance from the surface of the film can be detected and measured. In the absence of interference fringing from internal reflections, surface reflectance of the interface of the film with the surrounding air or vacuum is closely related to the refractive index of the film at its surface. Thus, surface reflection is monitored to provide a control signal to the deposition apparatus to conform the refractive index of material being deposited to a predetermined refractive index profile specified for the desired optical film.

14 Claims, 2 Drawing Sheets

REFRACTIVE INDEX MONITOR FOR DEPOSITION OF GRADIENT-INDEX FILMS

GOVERNMENT RIGHTS

The U.S. Government has rights in this invention under contract F33615-86-C-5051 awarded by the Department of the Air Force.

TECHNICAL FIELD

The present invention relates to the deposition of optical films on a substrate and, in particular, to a method of monitoring the refractive index of a thin film as it is being deposited.

BACKGROUND OF THE INVENTION

Optical thin films are important in the technology of coated optical surfaces. Optical coatings cause modifications in the transmitted and reflected intensities of light from interference that occurs when two or more beams of light are superimposed. If a film of a transparent substance having an appropriate thickness and refractive index is deposited on a lens, for example, the reflection of particular wavelengths of light from the lens surface can be almost completely suppressed. The light that otherwise would be reflected is not absorbed by such an antireflecting film; rather, the energy in the incident light is redistributed so that a decrease in reflection is accompanied by a corresponding increase in the intensity of the light that is transmitted. The beneficial effects of thin film coatings, such as antireflection, are so desirable that substantially all high quality optical components are provided with optical coatings.

Some advanced applications of optical technology have performance requirements that exceed the capabilities of conventional multiple layer thin films. New optical design procedures have been developed for these advanced applications to predict the continuous refractive index profile required for any desired transmission or reflection spectrum. These design techniques employ gradient index films, in which the index of refraction varies continuously as a function of depth into the film. Gradient index optical coatings have advantages over conventional technologies, including flexibility in filter design and increased stability in adverse environments. For example, the absence of discrete interfaces is predicted to lead to greater resistance to laser damage.

One type of gradient index structure is a rugate filter, the simplest manifestation of which has a periodic refractive index that varies sinusoidally with respect to optical thickness. A rugate filter is a gradient index analog of a quarterwave stack reflector. Compared to a quarterwave stack, however, a rugate filter has greatly suppressed high-frequency reflection harmonics. The rugate structure provides high reflectivity within a narrow bandwidth simply by increasing the number of periods in the filter.

Practical realizations of the rugate and other gradient index structures have been inhibited by the limitations of thin film fabrication technology. These limitations make it difficult to ensure that a fabricated coating accurately implements the theoretically specified refractive index profile. One prior method described in U.S. Pat. No. 4,707,611, which is incorporated herein by reference, measures the reflectance of two different wavelengths of light to determine the thickness and refractive index of an incremental thin film layer deposited on a base stack of layers. However, when a coating specification calls for a continuous refractive index profile, the thickness monitoring techniques of the prior art do not provide sufficient accuracy to ensure that the deposited layers will conform reliably to the specified profile. A slight error in the deposition thickness of a portion of a rugate filter, for example, can introduce a phase shift that may have a significant detrimental effect on the filter spectral structure. Also, an error in the refractive index of such a filter will add additional frequency components to the spectral profile, resulting in the generation of unwanted sidebands in the transmittance or reflectance spectrum. It is very difficult to compensate for such perturbations by any changes in the deposition of the remaining portion of the filter. Consequently, there is a need in the art for a method of directly monitoring and controlling the refractive index of a continuous gradient-index optical film while it is being deposited.

SUMMARY OF THE INVENTION

The present invention comprises a method of monitoring the refractive index of an optical thin film as it is being deposited on a substrate. The method is particularly suitable for monitoring and controlling the deposition of an optical film that requires a refractive index profile having a continuous gradient.

In the prior art, the refractive index of a gradient-index film is monitored indirectly by measuring optical thickness as the film is deposited. Generally, this is accomplished by detecting reflectance and noting turning points caused by interference between film surface reflection and film-substrate interface reflection. In the method of the present invention, reflectance of monitoring light from only the film surface is measured. Thus, reflection from the substrate or any internal layers of the film must be minimized, or else the desired surface reflection must be extracted from the interference pattern.

In a preferred embodiment of the present invention, the initial refractive index of the film is matched to the refractive index of the substrate. This may be accomplished by the incorporation of a quintic matching layer between the substrate and the optical film. The matching layer connects the two different index levels with a gradient-index that has zero slope at both ends. Used in this way, quintic matching layers have been shown to substantially eliminate reflection from the interface with the substrate. In addition to matching the substrate, the refractive index gradient of the film should not include rapid or abrupt changes that would produce internal reflections and cause interference. In a rugate, for example, another quintic may be impressed on the sine wave gradient over a few cycles at each so that the amplitude of the wave effectively begins and ends at zero. For greatest accuracy, the selected wavelength of monitoring light should be lower than the resonant wavelength of the gradient-index function to provide a more discriminating monitor.

The present invention comprises an easily performed method of real time deposition monitoring of the refractive index of a continuous, slowly varying gradient-index optical film. Within these parameters, the method requires only a measurement of reflectance in a wavelength band away from any resonances of the gradient-index function.

BRIEF DESCRIPTION OF THE DRAWINGS

For a more complete understanding of the present invention and for further advantages thereof, the following Description of the Preferred Embodiment makes reference to the accompanying Drawings, in which.

DETAILED DESCRIPTION OF THE INVENTION

In depositing a high performance optical coating with a continuously variable refractive index, it is of primary importance to control the refractive index of the coating precisely as a function of thickness of the coating. The present invention is a method of real time measurement of refractive index during deposition of a continuous gradient-index coating. If the refractive index of a film does not vary abruptly and the reflection from the film-substrate interface is eliminated, it has been discovered that the reflection of light from the surface of the film is due only to the value of the refractive index at the surface of the film.

In the present invention, reflectance monitoring is used to achieve a significant improvement in measurement and control of the refractive index of a thin film during the deposition process. This technique can best be explained by illustrating its application to the deposition of a rugate filter, a gradient index structure having a sinusoidal refractive index profile. Those skilled in the art, however, will appreciate that the invention is more broadly applicable to the deposition of any optical coating having a gradient refractive index.

Figure 1:
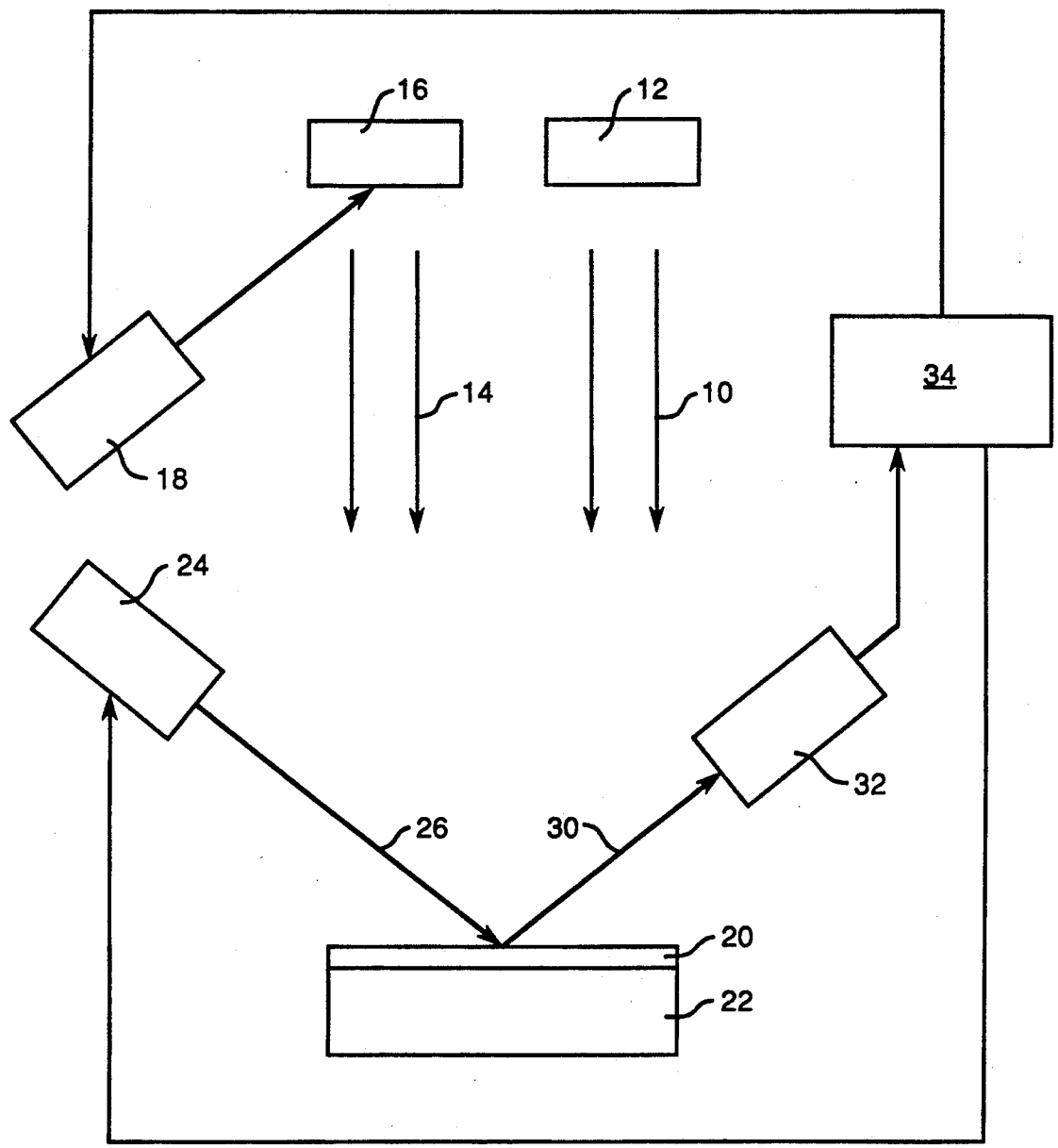
FIG. 1 is a schematic drawing of an optical film deposition and monitoring system of the present invention.

FIG. 1 is a schematic diagram illustrating a thin film deposition and monitoring apparatus that may be used to practice the present invention. A first dielectric material 10 is evaporated, as by electrical resistance heating, for example, from a first source of material 12. A second dielectric material 14 is evaporated from a second source of material 16 by a controllable source of energy 18, such as an electron beam gun. The evaporated materials 10 and 14 are codeposited in a thin film layer 20 on a substrate 22. Film 20 has a bottom surface that forms an interface with substrate 22 and a top surface distal substrate 22. A light source 24 is used to direct a beam of light 26 incident on film 20 and substrate 22. Light 30 reflected by film 20 is sensed by a detector 32. Preferably, the wavelength of light 26 is selected to be outside and lower than the reflection (stop) band of film 20 to provide a more discriminating monitor of the thin film coating.

A computer 34 is connected to control the deposition and monitoring apparatus. Prior to beginning the deposition of thin film layer 20, a predetermined refractive index profile specified for film 20 is stored in the memory of computer 34. Furthermore, controllable energy source 18 is calibrated so that the refractive index produced by the mixture of evaporated materials 10 and 14 codeposited on substrate 22 is a known function of the control signal provided by computer 34 to energy source 18. As the deposition process proceeds, computer 34 receives signals from detector 32 that correspond to the reflectance spectrum of film 20.

The typical rugate deposition process illustrated in FIG. 1 holds the rate of deposition constant for the low index material 10 and varies the rate for the high index material 14 so as to achieve the correct refractive index modulation in the deposited film. Detector 32 measures the reflectance of the top surface of film 20, and computer 34 uses the reflectance measurement to control the deposition rate of high index material 14, assuming a constant deposition rate of low index material 10. Those skilled in the art will note that this process is applicable to the control of a single evaporant as well as the relative rates of multiple evaporants.

In the method of the present invention, detector 32 monitors the Fresnel reflectivity of the interface of the top surface of film 20 with the surrounding air or vacuum. When the reflectance is due to the Fresnel surface reflectivity alone, the measured reflectance is effectively independent of the sub-surface gradient-index profile of film 20. The surface reflectance can be measured directly if any interfering reflections due to refractive index discontinuities, such as at the film-substrate interface, are minimized. This can be achieved, for example, by incorporating a quintic matching layer between the substrate and the gradient-index film. A quintic matching function, which may be approximated by a section of a sinewave, connects two refractive index levels by a curve that has zero slope at both ends. Such matching layers have been shown to eliminate substantially all reflection from the interfaces. The quintic layer should be matched smoothly to the substrate and to the gradient-index film. If the gradient-index is a sinusoid, the quintic may be matched to the top or bottom of the sinusoidal variation. Another method of matching the gradient-index is to apodize the amplitude of the sinewave function. For example, the quintic may be impressed on the sinewave index over a number of cycles at each end so that the wave starts and stops at an amplitude of near zero.

When all internal reflections are eliminated or greatly reduced, the only measurable reflection is the Fresnel reflection from the top surface of the film during deposition. As a result, the measured reflectance follows the refractive index of the film as it is being deposited. Therefore, the method of the present invention provides a real time refractive index monitor for gradient-index films that have profiles which do not vary abruptly. For this class of gradient-index films, the reflectance can be expressed as:

$$R=[(n-1)/(n+1)]^2,$$

where R is the currently measured reflectance and n is the value of the index of refraction of the film at the air or vacuum interface. Thus, the expression for the monitored index of refraction in terms of the measured reflectance is:

$$n = \frac{1 + \sqrt{R}}{1 - \sqrt{R}}.$$

Figure 2:
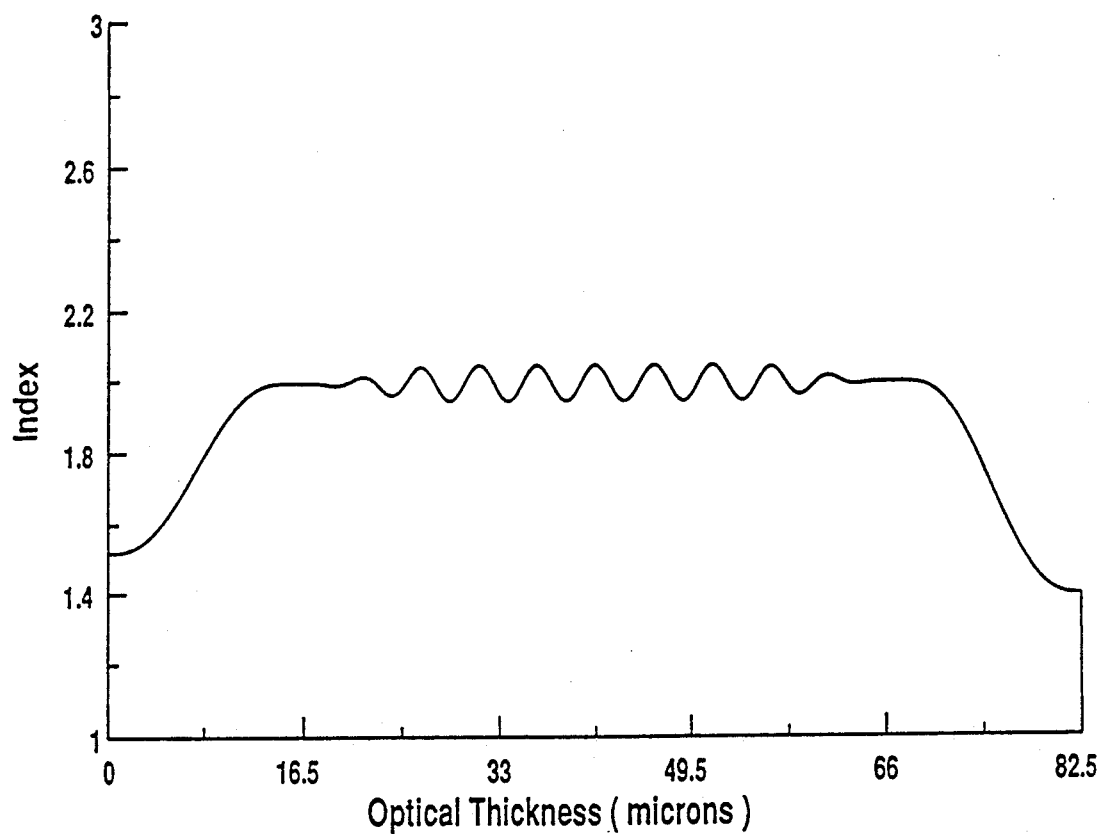
FIG. 2 is a plot of a refractive index profile for a 10.5 cycle rugate filter.

FIG. 2 is an example of a refractive index profile for a rugate filter having a sinusoidal index function of 10.5 cycles at 10 microns resonant wavelength. A monitor wavelength of 2 microns is selected because there are no side lobes or harmonics in the spectral reflectance of this structure at 2 microns wavelength. The amplitude of the sinewave is apodized by a quintic function over three cycles at each end of the sinewave. In addition, a quintic matching function connects the substrate (having an index of 1.52, on the left side of the profile) to the average of the sinewave index region. The sinewave function has an average index of 2.0 with an amplitude of 0.1. Another quintic (on the right side) terminates the gradient-index function at an index of 1.4 at the interface with the air.

Figure 3:
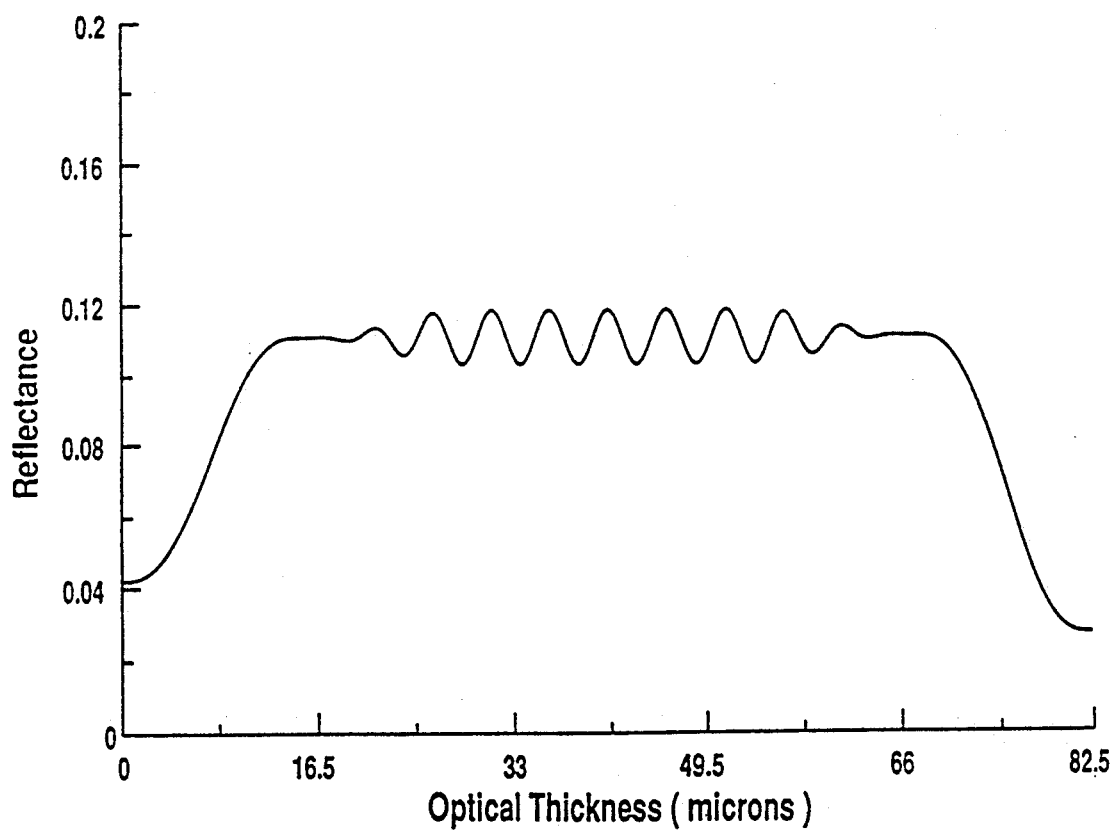
FIG. 3 is a plot of reflectance versus optical thickness detected by an optical monitor of the present invention during simulated deposition of the refractive index profile of FIG. 2.

Deposition of the gradient-index profile of FIG. 2 has been simulated by subdividing the index function into 660 thin homogeneous sublayers and using the characteristic matrix approach to evaluate the reflectance layer by layer. A plot of this reflectance is illustrated in FIG. 3, which simulates a monitor strip chart. The remarkable similarity between the index function of FIG. 2 and the reflectance of FIG. 3 is readily apparent. Applying the equation above to the reflectance data of FIG. 3 yields a monitored index that is nearly identical to the actual index function of FIG. 2.

The method of the present invention provides more accurate process control of gradient-index optical film deposition than prior methods because it monitors a characteristic (i.e. surface reflectance) that is very closely related to the refractive index of material actually being deposited. At present, the method is particularly suitable for monitoring the deposition of optical films having continuous refractive index profiles that initially match the index of the substrate and have no abrupt changes. In this class of films, interfering reflections from the substrate or internal discontinuities are minimized or eliminated so that only the surface reflectance is detected and measured. The method also may apply to optical films in general when used in conjunction with a method of extracting the surface refractive index from a reflectance pattern having interference fringing. In addition, it is contemplated that backside reflectance can be measured when using back illumination through the substrate. This procedure may reduce fogging and provide a bare substrate reflectance signal for periodic calibration of the system.

Although the present invention has been described with respect to a specific embodiment thereof, various changes and modifications may be suggested to one skilled in the art. Therefore, it is intended that the present invention encompass such changes and modifications as fall within the scope of the appended claims.

We claim:

1. A method of monitoring refractive index of a top surface of a gradient-index optical film as the film is being deposited on a substrate, comprising the steps of:
    illuminating the top surface of the film with light;
    detecting light reflected from only the top surface of the film;
    measuring said reflected light to determine reflectance of only the top surface of the film; and
    computing the refractive index of only the top surface of the film from said measured reflectance.

2. The method of claim 1, wherein the film comprises a rugate filter having a reflectance band, and the step of illuminating further comprises illuminating the top surface of the film with a monitoring wavelength of light selected to be outside and lower than said reflectance band.

3. The method of claim 1, further comprising the step of adjusting deposition of the optical film to produce a film having a refractive index gradient corresponding to a predetermined refractive index profile specified for the film.

4. The method of claim 3, wherein the step of adjusting deposition of the film further comprises the steps of:
    matching the refractive index of the film at the substrate with the refractive index of the substrate; and
    depositing the film with a continuous refractive index gradient.

5. The method of claim 4, wherein the step of matching comprises depositing a quintic matching layer joining the substrate to the film with a smoothly varying refractive index gradient.

6. The method of claim 1, wherein the step of computing comprises calculating the refractive index n from said measured reflectance R according to the formula $n = (1 + \sqrt{R})/(1 - \sqrt{R})$.

7. A method of depositing an optical film on a substrate, comprising the steps of:
    controlling a rate of deposition of optical material to form the optical film with a continuous refractive index gradient;
    illuminating a top surface of the film with light;
    detecting light reflected from only said top surface of the film;
    measuring reflectance of only said top surface of the film;
    computing a refractive index of only said top surface from said measured reflectance; and
    adjusting said rate of deposition of the optical material to conform said refractive index gradient to a predetermined refractive index profile specified for the film.

8. The method of claim 7, wherein the film comprises a rugate filter having a reflectance band, and the step of illuminating further comprises the step of selecting a monitoring wavelength of light lower than and outside said reflectance band.

9. The method of claim 7, wherein the step of controlling further comprises the steps of:
    matching the refractive index of the film at the substrate with the refractive index of the substrate; and
    depositing said optical material to provide the film with said continuous refractive index gradient.

10. The method of claim 9, wherein the step of matching comprises depositing a quintic matching layer having a smoothly varying refractive index gradient joining the substrate to the film.

11. The method of claim 7, wherein the step of computing comprises calculating the refractive index n from said measured reflectance R according to the formula $n = (1 + \sqrt{R})/(1 - \sqrt{R})$.

12. A method of monitoring and controlling deposition of an optical film having a continuous refractive index profile, comprising the steps of:
    depositing optical material on a substrate at a controllable rate to form the optical film atop the substrate, the film having a top surface and comprising a filter having a light reflectance band;
    selecting a monitor wavelength of light lower than and outside said reflectance band of the film;
    illuminating said top surface of the film with said monitor wavelength of light during deposition of the film;
    detecting light reflected from only said top surface of the film;
    measuring reflectance of only said top surface of the film;

computing a refractive index of only said top surface from said measured reflectance; and adjusting said controllable rate of deposition to conform the continuous refractive index profile of the film to a specified refractive index profile.

13. The method of claim 12, wherein the step of depositing optical material includes the step of depositing a quintic matching layer having a smoothly varying refractive index gradient joining the substrate to the film.

14. The method of claim 12, wherein the step of computing comprises calculating the refractive index n from said measured reflectance R according to the formula $n = (1 + \sqrt{R})/(1 - \sqrt{R})$.

* * * * *